United States Patent [19]

Schmitz et al.

[11] Patent Number: 5,222,983
[45] Date of Patent: Jun. 29, 1993

[54] IMPLANTABLE PROSTHESIS

[75] Inventors: Hermann-Joseph Schmitz, Berlin; Wolf D. Herold, Seefeld; Werner Zoellner, Steinebach-Woerthsee, all of Fed. Rep. of Germany

[73] Assignee: Thera Patent GmbH & Co., Seefeld, Fed. Rep. of Germany

[21] Appl. No.: 759,564

[22] Filed: Sep. 13, 1991

[30] Foreign Application Priority Data

Sep. 13, 1990 [DE] Fed. Rep. of Germany ... 9013067[U]
Jan. 4, 1991 [DE] Fed. Rep. of Germany ... 9100075[U]

[51] Int. Cl.$^5$ .......................... A61F 2/28; A61F 2/30; A61F 2/02; A61C 8/00
[52] U.S. Cl. ...................................... 623/16; 623/18; 623/11; 433/201.1
[58] Field of Search ..................... 623/16, 16 F, 1, 66, 623/18, 12; 433/2, 221, 224, 225, 226, 201.1

[56] References Cited

U.S. PATENT DOCUMENTS

| | | | |
|---|---|---|---|
| 3,855,638 | 12/1974 | Pilliar | 623/16 |
| 4,678,422 | 7/1987 | York | 623/5 |
| 4,729,766 | 3/1988 | Bergentz et al. | 623/1 |
| 4,865,603 | 9/1989 | Noiles | 623/16 |
| 4,923,467 | 5/1990 | Thompson | 623/5 |

FOREIGN PATENT DOCUMENTS

| | | |
|---|---|---|
| 0162604A1 | 4/1985 | European Pat. Off. . |
| 2181354A | 3/1988 | United Kingdom . |
| 2211416 | 7/1989 | United Kingdom ............. 433/201.1 |

Primary Examiner—Randall L. Green
Assistant Examiner—Dinh X. Nguyen
Attorney, Agent, or Firm—Foley & Lardner

[57] ABSTRACT

The shaft surface of a cementlessly implantable prosthesis is provided with a large number of holes which are formed as blind or pocket holes. Each hole is surrounded by a bulb in the form of a crater edge. The bony tissue that grows into the holes and around the bulbs ensures a firm seating of the prosthesis over a long time. The holes are preferably oriented in such a way that the bone pegs that extend into them can take up a desired load which may be either a compressive or a tensile force. A tensile force exerted on the bone will stimulate its growth.

9 Claims, 1 Drawing Sheet

IMPLANTABLE PROSTHESIS

BACKGROUND OF THE INVENTION

The invention relates to a cementlessly implantable prosthesis with a shaft the surface of which is provided with a large number of fine pocket holes. Prostheses of this type are used for replacing bones, dental roots, joints or rigid or flexible intervertebral discs.

Cementless implants avoid negative side effects arising from reactions of the organism with polymerizing cement components, which result in a destruction of the tissue and thus in a loosening of the implant.

As described in "Neuere Werkstoffe in der medizinischen Technik", Chemie-Ingenieur-Technik 47, No. 8 (1975), pp. 327–333 or in DE-A-2,721,686, known cementlessly implantable prosthesis are often provided with a porous surface which joins tightly with the bony tissue. According to DE-A-2,154,272, a porous structure may be obtained by sinter-fusing granules or beads onto the prosthesis shaft or by cutting small pocket holes into it by means of an electron or laser beam.

EP-A-0,321,389 describes the coating of a prosthesis with a biologically active ceramics material which may be resorbed, or with a resin which remains stable when exposed to the environment of living tissue. When the ceramics material is resorbed, a porous resin structure remains into which bony tissue may grow.

Anchoring a prosthesis is known to take some time until the bony tissue has grown into the porous surface. During this time, high loads must not be exerted on the prosthesis, and there is a danger of the prosthesis to come loose again.

SUMMARY OF THE INVENTION

It is an object of the invention to provide a prosthesis which can be easily implanted and which will quickly provide an anchoring in the bony tissue that can withstand high loads over a long lifetime.

This object is met by a cementlessly implantable prosthesis with a shaft the surface of which is provided with a large number of fine pocket holes wherein each of these holes is surrounded by a bulb formed in the shaft surface.

It has been found that the bony tissue grows relatively fast into a fine porous structure of this form. Particularly in cases where the toroidal bulbs are undercut, the prosthesis will be firmly seated in the bony tissue soon after implantation. The fine pocket holes may be provided directly in the shaft surface with no coating of the shaft being required. For this reason, there is no danger of prosthesis loosening due to an insufficient adherence of a coating.

In a preferred embodiment of the invention, at least part of the holes are so oriented that the axial direction pointing to the base of the hole forms an acute angle with the direction of the force exerted by said prosthesis on the bone under normal conditions. Due to this particular orientation of the fine pocket holes, compressive and tensile forces will be exerted by the surface of the prosthesis on the bone to cause a physiologic load on the bed of the implant. A loosening of the prosthesis in response to a damage of the bony tissue which has grown into the fine holes is thereby prevented.

According to Wolff's law of bone transformation, structural changes of a bone depend on the load exerted on the bone. Resorption occurs where compressive forces act on the bone, whereas tensile forces will result in bone growth. By correspondingly orienting the fine pocket holes, tensile forces can be exerted on the bone pegs that grows into the holes, thereby stimulating bone growth. In this case, the axial direction pointing to the base of the hole forms an acute angle with the force exerted by the prosthesis on the bone under normal conditions. At other places, however, the fine pocket holes may be oriented so that compressive forces act on the bone pegs.

A particularly firm and rapid anchoring of the prosthesis in the bone is achieved by providing about 20 to 100, preferably about 30 to 50, holes per $mm^2$ of shaft surface, each hole having a diameter of about 25 to 100 $\mu m$, preferably about 30 to 60 $\mu m$, and a depth of about 50 to 200 $\mu m$, preferably up to about 90 $\mu m$.

Shaping the shaft surface as a rounded thread will result in a tightly fitting connection between prosthesis and bone capable of withstanding high forces soon after implantation. This is due to the mechanical effect of the thread as well as to the enlarged surface as compared to that of a cylindrical shaft. Since a rounded thread has no sharp edges, irritations and peak stresses on the bony tissue are avoided. The implantation process is facilitated and a high-strength anchorage of the prosthesis is achieved by tapering the shaft from the head to the end of the prosthesis.

A titanium alloy is particularly suited as the material of the prosthesis due to its stability and biocompatability.

A practical way of producing the fine holes is by drilling or cutting them by a high-energy beam, such as produced by a laser, particularly an excimer laser.

DETAILED DESCRIPTION OF PREFERRED EMBODIMENTS

Figure 1:
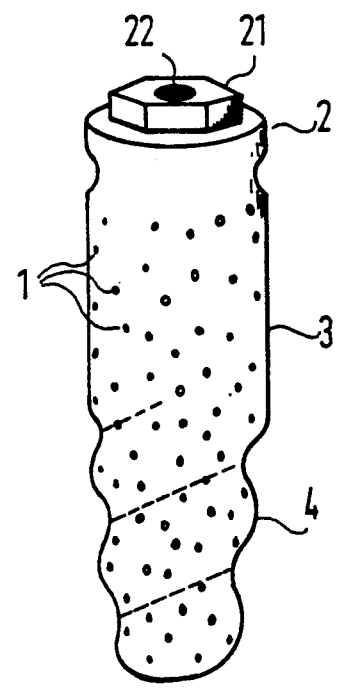
FIG. 1 shows a prosthesis constituting a dental implant.

The prosthesis depicted in FIG. 1 is a dental implant and includes a prosthesis head 2 and a shaft 3. A portion of the shaft 3 has a rounded screw thread 4 which provides not only a certain stability immediately after implantation but also an enlarged surface in contact with the bony tissue. Depending on the field of application, it may be more appropriate for the thread to extend along the whole shaft 3. In other cases the thread may be completely omitted. If the prosthesis is to be implantated into a jawbone, its shaft may advantageously be tapered with the cross-section decreasing from the head 2 to the end.

The prosthesis head 2 shown is provided with an internal screw thread for securing a dental prosthesis thereto. Further means for preventing a loosening of the structure screwed onto the head 2 are provided by a square or hexagonal portion 21 at the upper end of the head 2.

For enlarging the surface and ensuring a particularly safe support of the prosthesis, the lower portion of the shaft may be provided with macroscopic pins (not shown).

Blind or pocket holes 1 are formed in the shaft for anchoring the prosthesis in the bony tissue. These holes 1 may cover the whole shaft surface as shown in FIG. 1 or they may be provided only in certain surface areas in accordance with the desired transmission of forces between the prosthesis and the bone.

Figure 2:
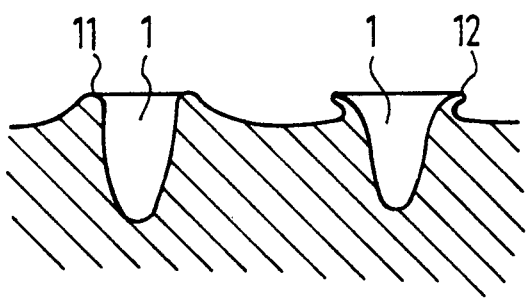
FIG. 2 is a cross-sectional view of two holes provided in the surface of the prosthesis shaft.

FIG. 2 shows a cross-section of an implant surface that has been irradiated by a laser (ELCS =Excimer Laser Conditioned Surface) resulting in holes 1 having a crater-shaped border or bulb 11, 12. The bulb 11, 12 is formed by material ejected from the hole during irradiation by the laser beam. Depending on the laser parameters (energy, beam diameter, exposure time, etc.) a simple bulb 11 or an undercut bulb 12 is formed.

Bony tissue that grows into the holes 1 and around the bulbs 11, 12 will achieve a double mechanical connection between the surface of the prosthesis and the surrounding bone bed of the implant. A particularly effective transmission of compressive as well as tensile forces is achieved by providing an undercut bulb 12.

Figure 3:
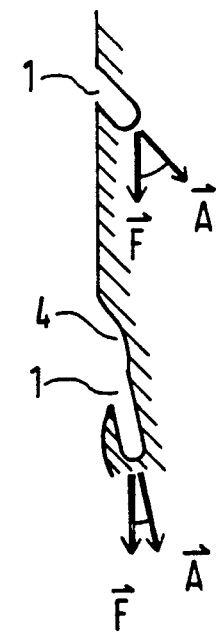
FIG. 3 is a diagram illustrating the forces acting upon the prosthesis.

FIG. 3 shows a cross-section of the anchorage of a prosthesis. In this example, the force $\vec{F}$ exerted on prosthesis and thus by the prosthesis on the bone is assumed to be parallel to the prosthesis surface. For stimulating the growth of bony tissue into the pocket holes 1, the holes are so oriented that the axial direction $\vec{A}$ pointing to the base of the hole forms an acute angle with the force $\vec{F}$. Thus, the bone pegs that grow into the holes are thus exposed substantially to tensile forces only. According to Wolff's law, their growth is thereby stimulated. The lower one of the two holes shown in FIG. 3 is arranged at an upper inclined surface portion of the thread 4. At this portion of the surface, the angle between the axial direction $\vec{A}$ and the force $\vec{F}$ may be made even more acute thereby enhancing the force component which stimulates the bone growth.

At those locations where the bone is naturally exposed to a compressive force, it may be meaningful to orient the fine holes in such a way that the bone pegs growing into the holes are similarly exposed to compressive forces.

EXAMPLE 1

A titanium surface measuring 3.2 mm $\times$ 6.25 mm (20 mm$^2$) was treated by an XeCl laser with an energy density of 16 J/cm$^2$. the treatment was performed for a period of 280 ns, and 25 pulses per hole were applied. A total of $38 \times 18 = 684$ pocket holes were produced each having a depth of approx. 60 $\mu$m and surrounded by a 40 to 50 $\mu$m high crater-shaped bulb of approx. 80 $\mu$m in width. Thus, the overall depth measured from the edge of the crater was approx. 100 $\mu$m.

EXAMPLE 2

Using an XeCl laser, $18 \times 38$ holes were bored into the test surface of Example 1 at an energy density of 10 J/cm$^2$, a treatment period of 15 ns and a pulse number of 402. Pocket holes with a slight downward tapering were generated which had a depth of approx. 100 $\mu$m and were surrounded by 40 to 60 $\mu$m high crater-shaped bulbs of approx. 70 $\mu$m in width.

What is claimed is:

1. An implantable prosthesis, comprising:
   a shaft having a bone engaging surface;
   a plurality of fine pocket holes, each of said holes having a top, a bottom, and a varying cross-sectional diameter, said holes being located in the bone engaging surface, said holes being closed at the bottom and open at the top, certain of said holes being generally bowl-shaped and generally circular in cross section from the bottom to the top of the hole, the cross-sectional diameter of the hole being smallest at the bottom of the hole and increasing toward the top of the hole, the hole at its top being surrounded by a relatively smooth and continuous crater-shaped bulb extending outwardly from said bone engaging surface, each bulb being larger in diameter than any other diameter of the hole.

2. The prosthesis of claim 1, wherein the holes have a diameter of about 25 to about 100 $\mu$m, and a depth of about 50 to 200 $\mu$m.

3. The prosthesis of claim 2, wherein the holes have a diameter of about 30 to about 60 $\mu$m, and a depth of about 50 to about 90 $\mu$m.

4. The prosthesis of claim 1, wherein the number of holes per mm$^2$ of the shaft surface is about 20 to about 100.

5. The prosthesis of claim 4, wherein the number of holes per mm$^2$ of the shaft surface is about 30 to about 50.

6. The prosthesis of claim 1, wherein under normal conditions a force is exerted by the prosthesis on a bone in a direction generally parallel to said surface of said shaft, and wherein at least a portion of said holes are oriented so that axes of the holes pointing to bases of the holes form acute angles with said direction of said force exerted by said prosthesis on said bone.

7. The prosthesis of claim 1, wherein the shaft surface is shaped as a rounded thread.

8. The prosthesis of claim 1, wherein the shaft is tapered with a shaft cross-section generally decreasing from a head to an end of the shaft.

9. The prosthesis of claim 1, wherein the shaft is made of a titanium alloy.

* * * * *